United States Patent [19]

Abeles et al.

[11] Patent Number: 5,066,643

[45] Date of Patent: Nov. 19, 1991

[54] FLUORINE AND CHLORINE STATINE OR STATONE CONTAINING PEPTIDES AND METHOD OF USE

[75] Inventors: Robert H. Abeles, Waltham, Mass.; Michael H. Gelb, Seattle, Wash.

[73] Assignee: Sandoz Ltd., Basle, Switzerland

[21] Appl. No.: 466,803

[22] Filed: Jan. 18, 1990

Related U.S. Application Data

[63] Continuation of Ser. No. 311,022, Feb. 14, 1989, abandoned, which is a continuation of Ser. No. 131,089, Dec. 10, 1987, abandoned, which is a continuation of Ser. No. 829,263, Feb. 14, 1986, abandoned, which is a continuation-in-part of Ser. No. 702,651, Feb. 19, 1985, abandoned.

[51] Int. Cl.$^5$ .................... A61K 37/02; C07K 5/10; C07K 7/06; C07K 7/08
[52] U.S. Cl. ........................ 514/18; 514/14; 514/15; 514/16; 514/17; 530/326; 530/327; 530/328; 530/329; 530/330
[58] Field of Search .............. 530/330, 329, 328, 327, 530/326; 514/18, 17, 16, 15, 14

[56] References Cited

U.S. PATENT DOCUMENTS 4,518,528 5/1985 Rasnick ........................... 530/300

FOREIGN PATENT DOCUMENTS 2531076 2/1984 France .

*Primary Examiner*—Lester L. Lee
*Attorney, Agent, or Firm*—Gerald D. Sharkin; Robert S. Honor; Thomas O. McGovern

[57] ABSTRACT

A peptide optionally in isosteric form wherein a methylene group in the backbone chain is disubstituted, one or both substituents being fluorine and/or chlorine, in free form or in pharmaceutically acceptable salt form, such as a compound of formula I

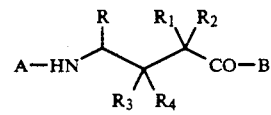

wherein the substituents have various significances, or an isosteric form thereof, is useful as an enzyme inhibitor. In particular, as a renin inhibitor, it is useful in the prophylaxis or treatment of hypertension and congestive heart failure.

It is prepared by a process comprising the step of coupling two corresponding peptide residues optionally in isosteric form, or precursors thereof, and if required appropriately converting any resultant compound in precursor form.

10 Claims, No Drawings

FLUORINE AND CHLORINE STATINE OR STATONE CONTAINING PEPTIDES AND METHOD OF USE

This is a continuation of application Ser. No. 07/311,022, filed Feb. 14, 1989, now abandoned, which in turn is a continuation of application Ser. No. 07/131,089, filed Dec. 10, 1987, now abandoned, which in turn is a continuation of application Ser. No. 06/829,263, filed Feb. 14, 1986, now abandoned, which in turn is a continuation-in-part of application Ser. No. 06/702,651, filed Feb. 19, 1985, now abandoned.

The present invention relates to novel peptides and peptide derivatives, their preparation and use and pharmaceutical compositions containing them.

The invention provides a peptide optionally in isosteric form wherein a methylene group in the backbone chain is disubstituted, one or both substituents being fluorine and/or chlorine, hereinafter referred to as "a compound of the invention".

The compounds of the invention are enzyme inhibitors. Depending on the nature of the peptide or peptide analogue, they may be used as inhibitors of various enzymes, e.g. of esterases, in particular lipases such as phospholipase A2, or of proteases such as: aspartyl proteases, in particular chymosin, renin, cathepsin D and pepsin; zinc-proteases, in particular angiotensin converting enzyme; aminopeptidases, in particular leucine aminopeptidase; thiol proteases, in particular papain; serine proteases, in particular elastase; carboxypeptidases, in particular carboxypeptidase A and B juvenile hormone esterase and acetylcholin esterase.

It is thus apparent that the peptides and peptide analogues of the invention have overall structures depending on the particular enzyme it is intended to inhibit. In general their structure is similar to the structure of known inhibitors and/or substrates for that particular enzyme. The fluorinated and/or chlorinated methylene group is generally most beneficial if it is located in the part or near the part on the inhibiting peptide or peptide analogue which corresponds to or reacts with the active site on the enzyme to be inhibited.

For example, as inhibitors of renin the compounds of the invention have an overall structure conveniently related to that of the specific determinant for the binding to the active site of renin in the renin substrate angiotensinogen.

The methylene group in the backbone chain defined above is preferably substituted by fluorine.

In particular the invention provides a compound as defined above wherein the fluorinated and/or chlorinated methylene group is part of a statine or statone, or of an isostere of a statine or statone, amino acid residue.

A preferred group of compounds of the invention is the compounds of formula I

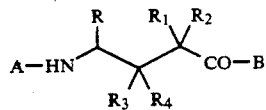

wherein
A is hydrogen or a substituent,
B is hydroxy or a further substituent with the proviso that one of A and B is a peptide residue,
$R_1$ is fluorine or chlorine,
$R_2$ is fluorine, chlorine or a further substituent, either $R_3$ is hydroxy, alkoxy or acyloxy and $R_4$ is hydrogen or $R_3$ and $R_4$ together are oxo and
R is hydrogen, alkyl, cycloalkyl, cycloalkylalkyl or an aryl, aralkyl, heteroaryl or heteroarylalkyl moiety optionally substituted in the aryl or heteroaryl part, or an isosteric form thereof.

$R_1$ preferably is fluorine. $R_2$ preferably is fluorine. $R_3$ preferably is hydroxy or together with $R_4$ oxo, it especially is together with $R_4$ oxo. R preferably is alkyl. A preferably is a substituent. B preferably is a further substituent.

A peptide residue consists of 1 or more amino acids. When there is more than one amino acid residue in a peptide residue they are normally linked by a peptidic carbamoyl group, i.e. by —CONH—.

A compound of the invention in isosteric form is for example a compound of the invention wherein one or more peptidic carbamoyl groups are in isosteric form, or wherein one or more amino acid residues are in the unnatural configuration when there is a natural counterpart.

A peptidic carbamoyl group in isosteric form is e.g. —CH₂NH— (reduced), —COCH₂— (keto), —CH(OH)CH₂— (hydroxy), —CH(NH₂)CH₂— (amino), —CH₂CH₂— or —CH₂CH₂CH₂— (hydrocarbon). Preferably a compound of the invention has no peptidic carbamoyl group in isosteric form overall. When it has peptidic carbamoyl groups in isosteric form it preferably has one or two, preferably one peptidic carbamoyl group in isosteric form.

Preferably a peptide residue consists of natural amino acid residues in their natural configuration. When there are amino acid residues in the unnatural configuration there preferably are only one or two amino acid residues, especially only one, in the unnatural configuration. Amino acid residue as used herein includes imino acid residues such as proline and hydroxyproline.

A peptide residue preferably is of 1 to 7 amino acid residues.

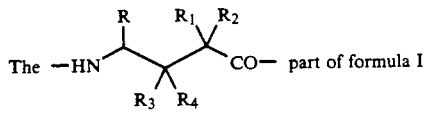

is the statine or statone or a derivative of the statine or statone amino acid residue. It preferably has the same configuration as natural statine at the carbon atom to which R is bound when this is asymmetrically substituted. The carbon atom to which $R_3$ and $R_4$ are bound preferably has the R configuration when it is asymmetrically substituted.

A further preferred group of compounds of the invention is the compounds of formula Ia

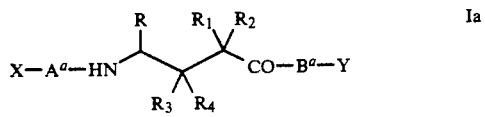

wherein
R and $R_1$ to $R_4$ are as defined above,
X is hydrogen or a peptide amino-end blocking group,
Y is hydroxy or a peptide carboxy-end blocking group, one of $A^a$ and $B^a$ is a peptide residue, the other is a bond or a peptide residue, or an isosteric form thereof.

X preferably is a peptide amino-end blocking group.

Y preferably is a peptide carboxy-end blocking group.

A peptide amino-end blocking group is e.g. alkoxycarbonyl of overall 2 to 10 carbon atoms, alkanoyl of overall 2 to 10 carbon atoms, cycloalkylcarbonyl of overall 4 to 8 carbon atoms, aroyl, or alkylsulfonyl of overall 1 to 10 carbon atoms, especially alkoxycarbonyl of overall 4 to 6 carbon atoms, particularly tert-butoxycarbonyl (BOC), or alkanoyl of overall 2 to 6 carbon atoms, particularly isovaleroyl (Iva). Cycloalkylcarbonyl preferably is of overall 4, 6 or 7 carbon atoms. Aroyl preferably is benzoyl. Alkylsulfonyl preferably is of 3 to 6 carbon atoms, it preferably is branched.

A peptide carboxy-end blocking group is e.g. alkoxy of 1 to 5 carbon atoms, amino, alkylamino of 1 to 5 carbon atoms, dialkylamino of independently 1 to 5 carbon atoms in the alkyl moieties thereof, (1-benzyl-piperidin-4-yl)-amino or (pyridin-2-yl)methylamino, in particular alkoxy of 1 to 5 carbon atoms, amino, alkylamino of 1 to 5 carbon atoms, (1-benzylpiperidin-4-yl)amino or (pyridin-2-yl)-methylamino, especially alkoxy of 1 to 3 carbon atoms, in particular methoxy or ethoxy.

Alkoxy preferably is of 1 to 5 carbon atoms, it especially is methoxy. Acyloxy preferably is of 2 to 6 carbon atoms, it especially is acetoxy.

Alkyl preferably is of 1 to 5 carbon atoms, it especially is branched, particularly isobutyl. Cycloalkyl preferably is of 3 to 7 carbon atoms, it especially is cyclopentyl or cyclohexyl. Cycloalkylalkyl preferably is of 3 to 7 carbon atoms in the cycloalkyl, particularly 5 or 6 carbon atoms, and of 1 to 5 carbon atoms, particularly 1 carbon atom, in the alkylene moieties thereof. Aryl preferably is phenyl. Aralkyl preferably is phenylalkyl of 7 to 12 carbon atoms, particularly benzyl. Heteroaryl preferably is pyridinyl, especially 4-pyridinyl, thienyl, especially 2-thienyl, or furyl, especially 2-furyl, preferably pyridinyl. Heteroarylalkyl preferably has 1 to 6 carbon atoms, especially 1 carbon atom in the alkylene moiety thereof. The heteroaryl moiety of heteroarylalkyl preferably has the significances indicated above as preferred for heteroaryl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, hydroxy or amino, particularly one hydroxy, amino, chlorine or bromine, optionally in protected form where appropriate.

A$^a$ and B$^a$ may e.g. have significances reported in the art to impart high affinity and selectivity in known enzyme inhibitors, such as, e.g. for renin inhibitors:

|  | a bond |
|---|---|
| for A$^a$: | —His— |
|  | —Phe— |
|  | —Leu— |
|  | —Phe—Phe— |
|  | -β-(1-naphthyl)-Ala— |
|  | —Val—Val— |
|  | —Phe—His— |
|  | —Pro—Phe—His— |
|  | —His—Pro—Phe—His— |
|  | —His—Phe—Pro—His—Leu— |
|  | —Pro—His—Pro—Phe—His— |

|  | -continued |
|---|---|
|  | a bond |
|  | and |
| for B$^a$: | —Ile— |
|  | —Leu— |
|  | —Val— |
|  | —Val—Phe— |
|  | —Val—Tyr— |
|  | —Leu—Phe— |
|  | —Ile—Phe— |
|  | —Ile—His— |
|  | —Ala—Phe— |
|  | —Phe—Phe— |
|  | —Leu—Tyr— |
|  | —Leu—Val—Phe— |
|  | —Val—Ile—His— |
|  | —Ile—His—Lys— |
|  | —Val—Ile—His—Lys— |
|  | and for pepsin inhibitors: |
| for A$^a$: | —Val— |
|  | —Val—Val— |
|  | and |
| for B$^a$: | —Ala— |

Alkoxycarbonyl preferably is of overall 4 to 6 carbon atoms, it preferably is branched, it especially is BOC. Alkanoyl preferably is of overall 2 to 6 carbon atoms, it preferably is branched, it especially is Iva. Cycloalkylcarbonyl preferably is of overall 4, 6 or 7 carbon atoms. Aroyl preferably is benzoyl. Alkylsulfonyl preferably is of 3 to 6 carbon atoms, it preferably is branched.

Glossary

BOC = tert-butoxycarbonyl
His = L-histidine
Iva = isovaleroyl
Ile = L-isoleucine
Leu = L-leucine
Lys = L-lysine
Phe = L-phenylalanine
Pro = L-proline
statine* = 4-amino-3-hydroxy-6-methylheptanoic acid
statone* = 4-amino-3-oxo-6-methylheptanoic acid
Tyr = L-tyrosine
Val = L-valine

*the absolute configuration is specifically indicated in the text.

A further preferred group of compounds of the invention is the compounds of formula Iaa $$X^a-A^{aa}-HN-\underset{R_3\ R_4}{\overset{R^a\ R_1\ R_2}{C}}-CO-B^{aa}-Y^a \quad \text{Iaa}$$

wherein $R_1$ to $R_4$ are as defined above;

$X^a$ is hydrogen, alkoxycarbonyl or alkanoyl of overall 2 to 10 carbon atoms, cycloalkylcarbonyl of overall 4 to 8 carbon atoms, aroyl, or alkylsulfonyl of overall 1 to 10 carbon atoms;

$Y^a$ is hydroxy, alkoxy of 1 to 5 carbon atoms, amino, alkylamino of 1 to 5 carbon atoms, dialkylamino of independently 1 to 5 carbon atoms in the alkyl moieties thereof, (1-benzylpiperidin-4-yl)amino or (pyridin-2-yl)methylamino, $R^a$ is hydrogen; alkyl of 1 to 5 carbon atoms; cycloalkyl of 3 to 7 carbon atoms; cycloalkylalkyl of 3 to 7 carbon atoms in the cycloalkyl and of 1 to 5 carbon atoms in the alkylene moieties thereof; phenyl or phenylalkyl of 7 to 12 carbon atoms optionally mono- or disubstituted in the phenyl ring by alkyl of 1 to 5 carbon atoms, alkoxy of 1 to 5 carbon atoms, halogen of atomic number of from 9 to 35, hydroxy or amino; pyridinyl, thienyl or furyl or pyridinylalkyl of 6 to 11 carbon atoms, thienylalkyl of 5 to 10 carbon atoms or furylalkyl of 5 to 10 carbon atoms; and one of $A^{aa}$ and $B^{aa}$ is a peptide residue of 1 to 15 amino acid residues, the other is a bond or a peptide residue of 1 to 15 amino acid residues, or an isosteric form thereof.

In a subgroup $Y^a$ is other than (pyridin-2-yl)methylamino.

A further group of compounds of the invention is the compounds of formula Iaaa

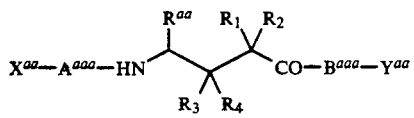

wherein $R_1$ to $R_4$ are as defined above, $X^{aa}$ is hydrogen, alkoxycarbonyl of overall 2 to 6 carbon atoms or alkanoyl of overall 2 to 6 carbon atoms, $Y^{aa}$ is hydroxy, alkoxy of 1 to 5 carbon atoms, amino, alkylamino of 1 to 5 carbon atoms, (1-benzylpiperidin-4-yl)-amino or (pyridin-2-yl)methylamino, $R^{aa}$ is alkyl of 1 to 5 carbon atoms, one of $A^{aaa}$ and $B^{aaa}$ is a peptide residue of 1 to 7 natural amino acids in their natural configuration, the other is a bond or a peptide residue of 1 to 7 natural amino acids in their natural configuration, or an isosteric form thereof.

In a subgroup the compounds are not in isosteric form. In a further subgroup $Y^{aa}$ is other than (pyridin-2-yl)methylamino. A further group of compounds of the invention is the compounds of formula Iaaaa

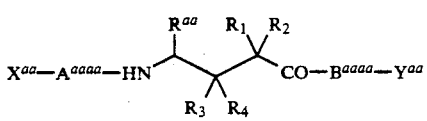

wherein
$R_1$ to $R_4$, $X^{aa}$, $Y^{aa}$ and $R^{aa}$ are as defined above,
$A^{aaaa}$ is a bond, —Val—, —His—Pro—Phe—His—, —Phe—Phe— or —Phe—His— and
$B^{aaaa}$ is a bond, —Ala—, —Leu—, —Val—, —Ile—, —Ile—Phe—, —Val—Phe—, —Ile—His— or —Leu—Phe—, with the proviso that at least one of $A^{aaaa}$ and $B^{aaaa}$ is other than a bond, or an isosteric form thereof.

In a subgroup the compounds are not in isosteric form. In a further subgroup $A^{aaaa}$ is a bond, —Phe—Phe— or —Phe—His—. In a further subgroup $B^{aaaa}$ is —Val—Phe—, —Ile—His— or —Leu—Phe—.

A compound of the invention may be in free form, e.g. amphoteric form, or in salt, e.g. acid addition, or anionic, salt form. A compound in free form may be converted into a salt form in known manner and vice-versa. Examples of salt forms are e.g. the trifluoroacetate, hydrochloride, sodium, potassium and ammonium salt forms.

A compound of the invention may be obtained by a process comprising the step of coupling two corresponding peptide residues optionally in isosteric form, or precursors thereof, and if required appropriately converting any resultant compound in precursor form.

The process is effected in a manner analogous to known methods. A precursor of a peptide residue is e.g. a compound in protected form, e.g. having a peptide amino and/or carboxy-terminal group which it is desired to split off or replace in the compound of the invention to be obtained, or some other functional group such as hydroxy which it is desired to convert into a further functional group such as oxo. A peptide residue may e.g. be a single amino acid residue depending on the length of the peptide to be obtained. The above applies mutatis mutandis to isosteric forms.

The coupling step is effected by general methods well known for peptide synthesis. It is e.g. effected in an inert solvent such as dimethylformamide. Preferably a temperature of from about 0° to about 25° C. is used. The presence of a base is preferred, e.g. - - - N-methylmorpholin.

The optional conversion step is also effected in a manner analogous to known methods. The oxydation of a hydroxy to a keto group is e.g. effected in an inert solvent such as methylene chloride. The oxidizing agent is e.g. chromium trioxyde dipyridinium complex. The reaction temperature may be from about 0° to about 50° C., preferably room temperature.

In particular a compound of formula Ia may be obtained by a process comprising coupling a corresponding compound of formula IIa

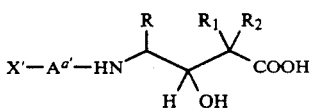

wherein
R, $R_1$ and $R_2$ are as defined above,
X' is a peptide amino-end protecting group and
$A^{a'}$ is a bond or a peptide residue, or an appropriate isosteric form thereof, and a corresponding compound of formula IIIa

wherein
Y' is a peptide carboxy-end protecting group and
$B^{a'}$ is a peptide residue, or an appropriate isosteric form thereof, or coupling a corresponding compound of formula IIb

wherein
X' is as defined above,
$A^{a''}$ is a peptide residue and
Z is a leaving group, or an appropriate isosteric form thereof, and a corresponding compound of formula IIIb

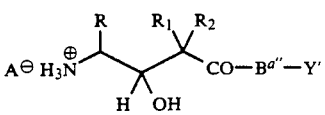

wherein
R, $R_1$, $R_2$ and Y' are as defined above,
$A^\ominus$ is an anion and $B^{a''}$ is a bond or a peptide residue, or an appropriate isosteric form thereof, and if required appropriately converting in the resultant compound the hydroxy moiety into the corresponding oxo moiety and/or splitting off any protecting group and/or replacing any protecting group by another group.

A peptide amino-end or carboxy-end protecting group is e.g. a group selected from the peptide amino-end or carboxy-end blocking groups defined above, insofar as appropriate.

X' preferably is alkoxycarbonyl of overall 2 to 2 carbon atoms, especially BOC. Y' preferably is alkoxy of 1 to 5 carbon atoms, especially methoxy. - - - Z preferably is $-N_3$. $A^\ominus$ preferably is the anion of a strong mineral acid, such as trifluoroacetate.

A compound of the invention may be isolated from the reaction mixture and purified in a manner analogous to known methods. Racemic and/or diastereoisomeric mixtures may be fractionated by known methods.

A compound used as a starting material may also be obtained in a manner analogous to known methods.

It is to be appreciated that when the fluorinated and/or chlorinated methylene group is part of an aminoacid unit based on statine, then the basic starting material for obtaining a compound of the invention is a corresponding statine substituted in the 2 position by fluorine and/or chlorine.

A compound of formula IIa may e.g. be obtained by reacting a corresponding compound of formula III

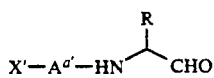                III wherein X', $A^{a'}$ and R are as defined above, with a corresponding compound of formula IV

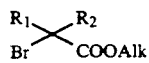    IV wherein $R_1$ and $R_2$ are as defined above and Alk is alkyl of 1 to 4 carbon atoms, preferably ethyl, and hydrolyzing the alkoxy group from the resultant ester.

Insofar as the preparation of any particular starting material is not particularly described, this may be effected in conventional manner or in analogous manner to that described herein.

In the following Examples all temperatures are in degrees Centigrade and are uncorrected.

EXAMPLE 1:
N—BOC—(4S,3R)-2,2-difluorostatin—Val—PheOCH3 (coupling)

727 mg N—BOC—(4S,3R)-2,2-difluorostatine, 800 mg H—Val—PheOMe hydrochloride and 630 mg N-hydroxybenzotriazole are dissolved in 5 ml dimethylformamide and 0.4 ml N-methylmorpholine are added. A solution of 480 mg dicyclohexylcarbodiimid in dimethylformamide is added at 0°. After 24 hours at room temperature the reaction mixture is taken up in ethyl acetate, washed with water, dried over potassium carbonate and evaporated to dryness. The residue is chromatographed over silicagel using ether/hexane as an eluent. The title compound is obtained (M.P. 105°–108°).

The starting material is obtained as follows:

a) 1.45 g zinc powder are suspended in 30 ml tetrahydrofuran and heated to reflux temperature. 4.4 g ethylbromodifluoroacetate are added at once and as soon as a vigorous reaction is initiated 2 g of N—BOC—L—leucinal dissolved in 5 ml tetrahydrofuran are added dropwise. After 30 minutes the reaction mixture is allowed to cool, then taken up in ethyl acetate and washed with 2N tartaric acid. The organic phase is dried over magnesium sulfate, evaporated to dryness and chromatographed over silicagel using ether/hexane 2:8 as an eluent. N—BOC—(4S,3R)-2,2-difluorostatine ethyl ester is obtained ($[\alpha]_D^{20} = -12.2°$, c=0.29 in ethanol).

b) 1 g N—BOC—(4S,3R)-2,2-difluorostatine ethyl ester is dissolved in methanol/water and reacted with 0.25 g of concentrated aqueous sodium hydroxide. After 2 hours the mixture is made acidic with 2N tartaric acid solution and extracted with ethyl acetate. The organic phase is dried over magnesium sulfate and evaporated to dryness. N—BOC—(4S,3R)-2,2-difluorostatine is obtained (crude).

EXAMPLE 2:
N—BOC—(4S)-2,2-difluorostaton—Val—PheOCH3 (precursor conversion by oxidation)

30 mg of the title compound of Example 1 are added to a solution of 90 mg chromium trioxyde dipyridinium complex in 20 ml methylene chloride. After 30 minutes at room temperature the reaction mixture is filtered over silicagel and the filtrate is evaporated to dryness. The residue is chromatographed over silicagel using ether/hexane as an eluent. The title compound is obtained.

EXAMPLE 3:
(4S,3R)-2,2-difluorostatin—Val—PheOCH3 trifluoroacetate (Precursor Conversion by Splitting off a Protecting Group)

1 g of the title compound of Example 1 is dissolved in 5 ml methylene chloride and reacted at 0° with 5 ml trifluoroacetic acid. After 30 minutes the mixture is evaporated to dryness under reduced pressure. Traces of trifluoroacetic acid remaining are eliminated by repeated azeotropic evaporation with benzene. The title compound is obtained (crude).

EXAMPLE 4:
N—BOC—Phe—His—(4S,3R)-2,2-difluorostatin—Val—PheOCH3 (coupling)

500 mg of the title compound of Example 3 and 420 mg of N—BOC—Phe—His—N3 are dissolved in 3 ml dimethylformamide, reacted with 0.1 ml N-methylmorpholine and allowed to stand at 0°–5° for 24 hours. The reaction mixture is taken up in ethyl acetate, washed with water, dried over potassium carbonate and evaporated to dryness. The residue is recrystallized from methanol/methylene chloride/ether. The title compound is obtained (M.P. 133°–136°).

| The following compounds of the invention a obtained in a manner analogous to Examples 1 to 4: | |
|---|---|
| Examples No. | Compound |
| 5[1)] | N—BOC—Phe—His-(4S)-2,2-difluorostaton-Val—Phe—OCH3 |

-continued

The following compounds of the invention a obtained in a manner analogous to Examples 1 to 4:

| Examples No. | Compound | |
|---|---|---|
| 6[2)] | Iva—Val-(4S)-2,2-difluorostaton-Ala—NH(3-methylbutyl) | Thin-layer chromatography: $R_f = 0.3$ (CHCl$_3$/CH$_3$COOC$_2$H$_5$) 1:1 |
| 7[3)] | Iva—Val-(4S,3R)-2,2-difluorostatin-Ala—NH(3-methylbutyl) | Thin-layer chromatography: $R_f = 0.7$ (CHCl$_3$/CH$_3$COOC$_2$H$_5$) 1:1 |
| 8 | N—BOC—Phe—Phe-(4S,3R)-2,2-difluorostatin-Leu—Phe—NH$_2$ | |
| 9 | N—BOC—Phe—Phe-(4S)-2,2-difluorostaton-Leu—Phe—NH$_2$ | |
| 10 | N—BOC—Phe—Phe-(4S,3R)-2,3-difluorostatin-Leu—NHN-benzyl | |
| 11 | N—BOC—Phe—Phe-(4S)-2,2-difluorostaton-Leu—NHN-benzyl | |
| 12 | N—BOC—Phe—Phe-(4S,3R)-2,2-difluorostatin-Val—Phe—OCH$_3$ | |
| 13 | N—BOC—Phe—Phe-(4S)-2,2-difluorostaton-Val—Phe—OCH$_3$ | |
| 14 | N—BOC—Phe—Phe-(4S,3R)-2,2-difluorostatin-Ile—His—OCH$_3$ | |
| 15 | N—BOC—Phe—Phe-(4S)-2,2-difluorostaton-Ile—His—OCH$_3$ | |
| 16 | Iva—His—Pro—Phe—His-(4S,3R)-2,2-difluorostatin-Ile—Phe—OCH$_3$ | |
| 17 | Iva—His—Pro—Phe—His-(4S)-2,2-difluorostaton-Ile—Phe—OCH$_3$ | |
| 18[4)] | (4S,3R)-2,2-difluorostaton-Ala—NH(3-methylbutyl)trifluoroacetate | |
| 19[6)] | N—BOC-(4S,3R)-2,2-difluorostatin-Ala—NH(3-methylbutyl) | $R_f = 0.15$(ethyl acetate hexane 3:7) |
| 20[5)] | N—BOC-(4S)-2,2-difluorostaton-Ala—NH(3-methylbutyl) | |

[1)]Starting from the compound of Example 4, analogous to Example 2
[2)]Starting from the compound of Example 7, analogous to Example 2
[3)]Starting from the compound of Example 18, analogous to Example 4, by reaction with Iva—Val—OH (M.P. 196-198°); the latter compound is prepared by reaction of isovaleric acid with L-valine ethyl ester hydrochloride in dimethylformamide in the presence of 4-methylmorpholine and isobutylchloroformate
[4)]Starting from the compound of Example 19, analogous to Example 3
[5)]Starting from the compound of Example 19, analogous to Example 2
[6)]Starting from the compound of Example 1a), analogous to Example 1, by reaction with L-alanyliso-amylamide acetate (M.P. 102-104°) in chloroform. The latter compound is prepared by reaction of N-(benzyloxycarbonyl)-L-alanyl isoamylamide (M.P. 107-108°) in acetic acid and methanol with hydrogen over 10% Pd—C.

The compounds of the invention are useful because they possess pharmacological activity.

In particular they exhibit effects typical of enzyme inhibitors. The inhibitory activity with respect to a particular enzyme is of course dependent on the overall peptidic structure. Thus, those compounds defined above particularly suited as inhibitors of renin activity exhibit a 50% inhibition of mouse submaxillary gland renin activity on the synthetic octapeptide substrate at a concentration from $10^{-5}$M to $10^{-11}$M in the test method of K Murakami et al; Analyt.Biochem. 110 (1981) 232-239 (with the modification that the concentration of synthetic substrate is lowered from 20 µM to 7 µM), and in the method of P. Corvol et al; Biochem.Biophys.Acta 523 (1978) 485-493.

In the antibody trapping method of K. Poulsen and J. Jørgensen, J.Clin.Endocrin.Metab. 39 (1974) 816-825 they inhibit human plasma renin activity at a concentration ranging from $10^{-5}$M to $10^{-11}$M.

The compounds of the invention are therefore useful for the prevention and treatment of conditions characterized by an etiology involving an enzyme disfunction and for which an inhibition of enzymatic activity is indicated.

For example, as renin inhibitors they are useful for the prevention and treatment of hypertension and congestive heart failure.

As elastase inhibitors they are useful for the prevention and treatment of general inflammation, emphysema, arthritis and degeneration of the elastic tissues resulting from e.g. infection.

The compounds of Examples 6 and 7 inhibit pepsin with $K_i$ values of, respectively, $6 \times 10^{-11}$M and $5 \times 10^{-10}$M.

Preferred among the compounds of the invention wherein the fluorinated and/or chlorinated methylene group is part of a statine or statone, or of an isosteric form of a statine or statone amino acid unit are those compounds based on statone. Also preferred are those compounds wherein the methylene group is fluorinated, particularly difluorinated.

Preferred for the prevention and treatment of hypertension and congestive heart failure are the title compounds of Examples 4 and 5, particularly of Example 5.

For the above-mentioned uses the dosage will, of course, vary depending on the compound employed, mode of administration and treatment desired. In general, satisfactory results are obtained when administered at a daily dosage of from about 0.02 mg/kg to about 10 mg/kg animal body weight. For the larger mammal an indicated total daily dosage is in the range of from about 1 mg to about 500 mg conveniently given in divided doses 2 to 4 times a day in unit and dosage form containing for example from about 0.25 mg to about 250 mg of the compounds admixed, or in sustained release form.

The compounds may be administered in similar manner to known standards for use in these utilities, for example, in hypertension, captopril. The suitable daily dosage for a particular compound will depend on a number of factors such as its relative potency of activity. It is therefore indicated that the compounds may be administered at similar dosages than conventionally employed for known standards.

The compounds of the invention may be administered in free form or in pharmaceutically acceptable salt form. Such salt forms exhibit the same order of activity as the free forms and are readily prepared in conventional manner. The present invention also provides a pharmaceutical composition comprising a compound of the invention in free form or in pharmaceutically acceptable salt form, in association with a pharmaceutical carrier or diluent. Such compositions may be formulated to be used for enteral, preferably oral, administration, e.g. tablets, or parenteral administration, e.g. injectable solutions or suspensions. The compounds of Examples 1 to 5 and 8 to 17 are more particularly suited as renin inhibitors. The compounds of Examples 6, 7 and 18 to 20 are more particularly suited as pepsin inhibitors.

We claim:

1. A compound of formula Ia

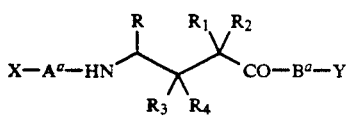

Ia wherein $R_1$ and $R_2$ are independently fluorine or chlorine, $R_3$ is hydroxy, alkoxy or acyloxy and $R_4$ is hydrogen or $R_3$ and $R_4$ together are oxo, R is hydrogen, alkyl, cycloalkyl, cycloalkylalky, aryl, aralkyl, pyridinyl, pyridinylalkyl, thienyl, thienylalkyl, furyl, or furylalkyl optionally substituted in the aryl, pyridinyl, thienyl, or furyl ring, X is hydrogen or a peptide amino-end blocking group, Y is hydroxy or a peptide carboxy-end blocking group, and $A^a$ and $B^a$ are independently a peptide residue containing 1 to 7 natural amino acids, or an isoteric form thereof, in free form or in pharmaceutically acceptable salt form.

2. A compound according to claim 1, in which

X is hydrogen, alkoxycarbonyl or alkanoyl of 2 to 10 carbon atoms, cycloalkylcarbonyl of 4 to 8 carbon atoms, aroyl, or alkylsulfonyl of 1 to 10 carbon atoms;

Y is hydroxy, alkoxy of 1 to 5 carbon atoms, amino, alkylamino of 1 to 5 carbon atoms, dialkylamino of independently 1 to 5 carbon atoms in the alkyl moieties thereof (1-benzylpiperidin-4-yl)amino or (pyridin-2-yl)methylamino; and R is hydrogen, alkyl of 1 to 5 carbon atoms; cycloalkyl of 3 to 7 carbon atoms; cycloalkylalkyl of 3 to 7 carbon atoms in the cycloalkyl and of 1 to 5 carbon atoms in the alkylene moieties thereof; phenyl or phenylalkyl of 7 to 12 carbon atoms optionally mono- or disubstituted in the phenyl ring by alkyl of 1 to 5 carbon atoms, alkoxy of 1 to 5 carbon atoms, halogen of atomic number of from 9 to 35, hydroxy or amino; pyridinyl, thienyl or furyl or pyridinylalkyl of 6 to 11 carbon atoms, thienylalkyl of 5 to 10 carbon atoms or furylalkyl of 5 to 10 carbon atoms; in free form in pharmaceutically acceptable salt form.

3. A compound according to claim 1 in which

X is hydrogen, alkoxycarbonyl of 2 to 6 carbon atoms or alkanoyl of 2 to 6 carbon atoms, Y is hydroxy, alkoxy of 1 to 5 carbon atoms, amino, alkylamino of 1 to 5 carbon atoms, (1-benzylpiperidin-4-yl)-amino or (pyridin-2-yl) methylamino, and R is alkyl of 1 to 5 carbon atoms, in free form or in pharmaceutically acceptable salt form.

4. A compound according to claim 1 in which $A^a$ is —Val—, —His—Pro—Phe—His—, —Phe—Phe— or —Phe—His—, and $B^a$ is —Ala—, —Leu—, —Val—, —Ile—, —Ile—Phe—, —Val—Phe—, —Ile—His— or —Leu—Phe—, ps in free form or in pharmaceutically acceptable salt form.

5. The compound of claim 1 which is N—BOC—Phe—His—(4S,3R)-2,2-difluorostatin—Val—PheOCH$_3$, in free form or in pharmaceutically acceptable salt form.

6. The compound of claim 1 which is N—BOC—Phe—His—(4S)-2,2-difluorostaton—Val—PheOCH$_3$, in free form or in pharmaceutically acceptable salt form.

7. The compound of claim 1 which is Iva—Val—(4S)-2,2-difluorostaton—Ala—NH(3-methylbutyl), in free form or in pharmaceutically acceptable salt form.

8. A pharmaceutical composition comprising a therapeutically effective amount of a compound of claim 1 in free form or in pharmaceutically acceptable salt form, in association with a pharmaceutical carrier or diluent.

9. A method of inhibiting protease and esterease enzymatic activity which comprises administering to an animal in need of such treatment a therapeutically effective amount of a compound of claim 1.

10. A method of preventing or treating hypertension or congestive heart failure which comprises administering to an animal in need of such treatment a therapeutically effective amount of a renin-inhibiting compound of claim 1.

* * * * *